US008604251B2

(12) United States Patent
Berens et al.

(10) Patent No.: US 8,604,251 B2
(45) Date of Patent: Dec. 10, 2013

(54) OLIGOFUNCTIONAL PHOTOINITIATORS

(75) Inventors: Ulrich Berens, Binzen (DE); Jean-Luc Birbaum, Binningen (CH); Katia Studer, Rixheim (FR)

(73) Assignee: BASF SE, Ludwigshafen (DE)

( * ) Notice: Subject to any disclaimer, the term of this patent is extended or adjusted under 35 U.S.C. 154(b) by 179 days.

(21) Appl. No.: 13/256,947

(22) PCT Filed: Mar. 19, 2010

(86) PCT No.: PCT/EP2010/053607
§ 371 (c)(1),
(2), (4) Date: Oct. 10, 2011

(87) PCT Pub. No.: WO2010/108862
PCT Pub. Date: Sep. 30, 2010

(65) Prior Publication Data
US 2012/0029107 A1    Feb. 2, 2012

(30) Foreign Application Priority Data

Mar. 24, 2009   (EP) .................................... 09156044

(51) Int. Cl.
| C07C 49/00 | (2006.01) |
| C07C 49/12 | (2006.01) |
| C07C 49/15 | (2006.01) |
| C07C 49/17 | (2006.01) |
| C08F 2/50  | (2006.01) |
| C08J 3/28  | (2006.01) |

(52) U.S. Cl.
USPC ........... 568/331; 568/303; 568/308; 568/309; 568/319; 568/323; 522/36; 522/35; 522/113; 522/114; 522/184

(58) Field of Classification Search
USPC .............. 522/35, 36, 113, 114, 184; 568/303, 568/308, 309, 319, 323, 331
See application file for complete search history.

(56) References Cited

U.S. PATENT DOCUMENTS 7,462,650 B2 * 12/2008 Sommerlade et al. .......... 522/36
2006/0270748 A1    11/2006 Sommerlade et al.

FOREIGN PATENT DOCUMENTS

WO    2004/099262 A    11/2004

OTHER PUBLICATIONS

Buu-Hoi Ng., Justus Liebeigs Annalen Der Chemie, vol. 556 (1943) pp. 1-9.
Chemische Berichte, vol. 119, pp. 3422-3431 (1986).

* cited by examiner

Primary Examiner — Sanza McClendon
(74) Attorney, Agent, or Firm — Tyler A. Stevenson (57) ABSTRACT

The invention pertains to novel oligofunctional photoinitiators of the formula (1) or (1A). $R_1$ and $R_2$ are methyl or together are $-(CH_2)_5-$; and n is 2 or 3, and the solvent in (1A) is water or an organic solvent; and their use in photopolymerizable compositions, in particular inks.

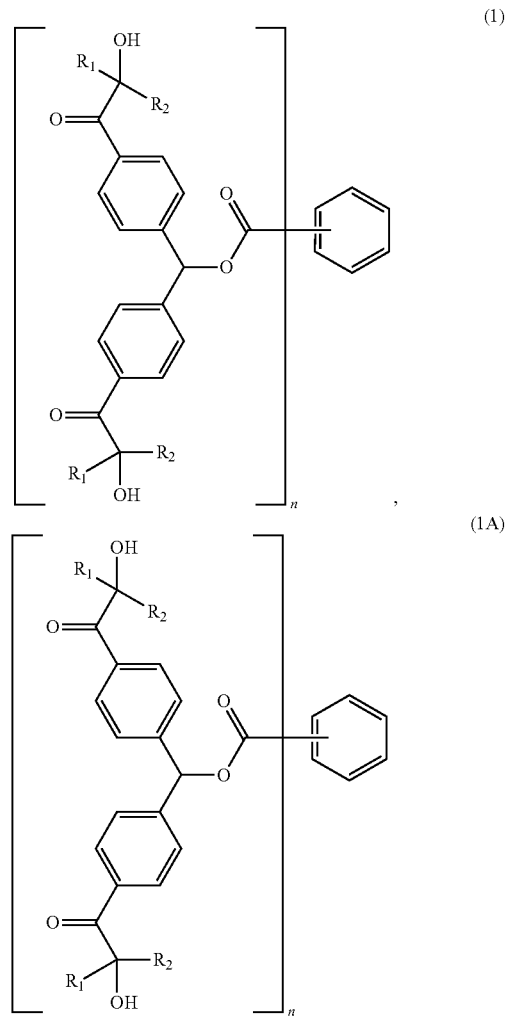

16 Claims, 1 Drawing Sheet

Fig. 1: X-ray powder spectrum of the product of example 3b

Fig. 2: X-ray powder spectrum of the product of example 3c:

OLIGOFUNCTIONAL PHOTOINITIATORS

The invention pertains to a novel hig-molecular photoinitiator and a process for its preparation as well as its use in photopolymerizable compositions, in particular in printing-inks.

Radiation-curable systems can be used in a large number of applications, for example in overprint coatings, printing inks, in the manufacture of electronic printed circuit boards and printing plates, and in the coating of various substrates, such as wood, plastics, paper, glass or metal. For efficient polymerisation of such systems, it is necessary to use a photoinitiator, from which, as a result of interaction with electromagnetic radiation, reactive particles such as free radicals or cations (protons) are generated. A disadvantage of most of the initiators frequently used in practice is the undesirable odour that is produced when they are used. There is therefore a demand in the art for low-odour, low-volatility photoinitiators. Moreover, the photoinitiator should be available in an easy-to-handle form, should cause minimal yellowing of the cured film, and should be readily soluble in radiation-curable systems.

Accordingly, there is a need in the art for low-odour, low-volatility photoinitiators that can be used in said radiation-curable overprint coatings, printing inks, and in the coating of various substrates, such as wood, plastics, paper, glass or metal. In addition, it is desirable for the photoinitiator to contribute towards an improved crosslinking density and to produce fewer photolysis products that are capable of migration. This latter criterion is particularly important for applications related to food packaging. Moreover, the photoinitiator should be available in an easy-to-handle form, should cause minimal yellowing of the cured film, and should be readily soluble in radiation-curable systems.

A further important criterion for the use of photoinitiators is the efficiency with which the reactive constituents of the formulation are polymerised. This has a direct influence on the cure speed which can be achieved during use, and on the degree of crosslinking of the resulting polymer.

It is known from WO2004/099262 that bis[4-(2-hydroxy-2-methylpropionyl)phenyl]methanol, [CAS-Regno 793686-13-2], can react at the secondary hydroxylic group with isocyanates to give urethanes that are active low-odor, low volatile photoinitiators. However, preparation of [793686-13-2] according to that patent application requires irradiation with light or/and use of carbon tetrachloride as a solvent during the bromination of its precursor 2-chloro-1-{4-[4-(2-chloro-2-methyl-propionyl)-benzyl]-phenyl}-2-methyl-propan-1-one. Moreover, it is well known that isocyanate groups can participate in different secondary reactions such as dimer (uretdione) or trimer (isocyanurate) formation (as mentioned, for example, in International Journal of Adhesion & Adhesives 2007, vol. 28, p. 29), which can lead to complications during the purification of the desired reaction products.

Therefore, there is still a need for low-odor, low volatile, high efficiency photoinitiators that can be conveniently prepared.

Subject of the invention therefore is a compound of formula (1) or (1A)

(1)

(1A)

wherein
$R_1$ and $R_2$ are methyl or together are $—(CH_2)_5—$; and
n is 2 or 3, and the solvent in (1A) is water or an organic solvent.

Preferred is a compound of the formula (1) or (1A) as described above, wherein $R_1$ and $R_2$ are methyl.

The groups are for example linked to the phenyl ring in 1,3,5-position, in 1,4-position, in 1,2-position, preferably in 1,4-position.

Interesting are the compounds of the formula (1) or (1A), wherein n is 2.

In case that $R_1$ and $R_2$ together are —$(CH_2)_5$— the following structure is formed:

wherein n is as defined above.

Preferred compounds are

The compounds of the present invention can for example be prepared from bis[4-(2-hydroxy-2-methylpropionyl)phenyl]methanol (WO2004/099262) by esterification of the secondary hydroxyl group with phthaloyl chloride, isophthaloyl chloride, or trimesoyl chloride in the presence of a base, for example, a tertiary amine such as triethylamine or pyridine in an organic solvent, for example, toluene, diethyl ether, tetrahydrofuran, dimethylformanide at temperatures between −30 to 100° C., preferably −15 to +40° C.

Alternatively, they can be obtained by reaction of the same alcohol with the corresponding acids in the presence of a suitable reagent in catalytic or stoechiometric amount. There are many catalysts described in all standard organic chemistry textbooks, for instance, in J. March, Advanced Organic Chemistry, Wiley, 1992, $4^{th}$ Ed, pp. 393-396. Very common catalysts are mineral acids, for example, sulfuric acid, or organic acids, for example, 4-toluenesulfonic acid. Removal of water can be effected, for example, by azeotropic distillation. Dehydrating agents, for example, dicyclohexylcarbodiimide or molecular sieves can also be used. Other reagents and conditions suitable for esterification of the hydroxyl group of benzhydrol have also been proposed, for example, phosphorus triphenylphosphine and bromine in the presence of pyridine (Japanese patent application JP56150092 A), or cyanuric chloride (Heterocycles 1990, 31, 2055). There are also known reagents for selective esterification of secondary alcohols in the presence of tertiary alcohols, such as di-2-pyridyl thionocarbonate in the presence of 4-dimethylaminopyridine (Chemistry Letters 1998 p. 679). Suitable solvents and temperatures for the reaction are well known. For example, solvents forming azeotropes with water, such as toluene, m-xylene, cyclohexane, cyclopentanone can be used. Temperatures at the boiling point of the azeotrope, for example 40-120° C., are suitable for the reaction.

Transesterification of $C_1$-$C_4$-alkyl esters of terephthalic, isophthalic, and mesitoic acids with bis[4-(2-hydroxy-2-methylpropionyl)phenyl]methanol is also possible. Such transesterification can be carried out in various solvents, for example, in those solvents forming an azeotrope with the alcohol to be removed. Suitable solvents are, for example, acetone, toluene, dioxane, cyclohexane, chlorobenzene, m-xylene and the like. Temperatures at the boiling point of the azeotrope, for example 40-120° C., are suitable for the reaction. There is a wide range of catalysts suitable for transesterification known to the person skilled in the art. In many cases it is advantageous to use a catalyst which facilitates the transesterification reaction and allows the use of lower temperatures. Useful catalysts are for example Lewis or Brönsted acids, Lewis or Brönsted bases or nucleophiles or metal salts (see for example A. G. Grasa et al., Synthesis (2004), (7), 971; J. Otera et al., Acc. Chem. Res. (2004), 37, 288; H. E. Hoydonckx et al. Topic in Catalysis (2004), 27, O. A. Mascaretti et al. Aldrichimica Acta (1997), 30, 55; R. Sridharan et. al. J. Scient. & Indust. Research (1974), 33, 178). Suitable enzymes are also frequently used to facilitate transesterification reactions (see for example E. Santaniello et al. Current Org. Chem. (2006), 10, 1059; S. Negishi, Handbook of Industrial Biocatalysis, CRC Press, (2005), 12/1-12/14; H. J. Altenbach, Nachrichten aus Chemie, Technik, and Laboratorium (1988), 36(10), 1114).

Subject of the invention therefore also is a process for the preparation of a compound of the formula (1) as defined above, wherein n compounds of the formula (2)

(2)

wherein n, $R_1$ and $R_2$ are as defined above,
are reacted with an acid chloride of the formula (3)

(3)

wherein n is as defined above,
in the presence of a base, in particular triethyl amine, to give a compound of the formula (1);
and subsequent crystallization from a solvent to give the compound of the formula (1A).

The compounds of the formula (1A) are prepared from the compounds of the formula (1) by crystallisation from an appropriate solvent, such as for example water or acetic acid ethyl ester, preferably acetic acid ethyl ester.

As mentioned above, the intermediate bis[4-(2-hydroxy-2-methylpropionyl)phenyl]methanol can be obtained according to a method described in WO2004/099262.

Several procedures for the benzylic bromination of the isomeric mixture of 2-chloro-1-{4-[4-(2-chloro-2-methyl-propionyl)-benzyl]-phenyl}-2-methyl-propan-1-one and 2-chloro-1-{4-[3-(2-chloro-2-methyl-propionyl)-benzyl]-phenyl}-2-methyl-propan-1-one to give the corresponding mixture of 1-(4-{bromo-[4-(2-chloro-2-methyl-propionyl)-phenyl]-methyl}-phenyl)-2-chloro-2-methyl-propan-1-one and 1-(4-{bromo-[3-(2-chloro-2-methyl-propionyl)-phenyl]-methyl}-phenyl)-2-chloro-2-methyl-propan-1-one have been described in WO2004/099262.

Example 2a of WO 2004/099262 discloses the enol-chlorination and subsequent benzylic bromination of a solution of the isomeric mixture of bis[4-(2-methyl-propionyl)-phenyl]-methane and [3-(2-methyl-propionyl)-phenyl]-[4-(2-methyl-propionyl)-phenyl]-methane in ortho-dichlorobenzene under the irradiation of light. The bromination procedure is suitable for the preparation of small quantities of the product, but on scale-up the use of lamps becomes expensive, and the necessity of irradiation with light causes problems such as the formation of intransparent films on the well of immersed lamps. Moreover, the uptake of bromine is sluggish and requires prolonged reaction times as well as an excess of bromine. Removal of the solvent ortho-dichlorobenzene by steam distillation also adds considerable costs to the product on larger scale. After workup the product is obtained in two crops amounting to a combined yield of 38%.

Example 2b (from WO 2004/099262) describes the enol-chlorination and subsequent benzylic bromination of a solution of the isomeric mixture bis[4-(2-methyl-propionyl)-phenyl]-methane and [3-(2-methyl-propionyl)-phenyl]-[4-(2-methyl-propionyl)-phenyl]-methane in carbon tetrachloride. Again, for the bromination irradiation with light is required, and an excess of bromine is required in order to achieve complete conversion of the starting material. Here, the product is obtained in several crops amounting to 77% yield; however, this material is contaminated with the product resulting from double benzylic bromination.

Surprisingly, it was found that a bromination of a solution of 2-chloro-1-{4-[4-(2-chloro-2-methyl-propionyl)-benzyl]-phenyl}-2-methyl-propan-1-one and 2-chloro-1-{4-[3-(2-chloro-2-methyl-propionyl)benzyl]-phenyl}-2-methyl-propan-1-one in ortho-dichlorobenzene as obtained from the enol chlorination as described in example 2a in WO 2004/099262 at elevated temperatures can be achieved without the need of irradiation with light and without using an excess of bromine. Moreover, the bromination proceeds also in the absence of radical initiators such as azobisisobutyronitrile (AIBN) or dibenzoyl peroxide, which are typically added to such bromination reactions. After partial removal of the solvent ortho-dichlorobenzene in vacuum and addition of hexane, the product is obtained as a single crop in 84% yield. Surprisingly, neither the product resulting from double benzylic bromination nor from bromination of the aromatic nucleus is contained in the product. Also, no substitution of the chlorine atoms by bromine is observed.

Subject of the invention therefore also is a process for the preparation of a compound of the formula (2)

(2)

wherein $R_1$ and $R_2$ are as defined above;
in which process step 1
a compound of formula (4)

(4)

wherein $R_1$ and $R_2$ are as defined above;
is treated with bromine without irradiation with lamps or the need to add radical initiators to give a the brominated compound of the formula (5)

(5)

wherein $R_1$ and $R_2$ are as defined above; and
in which process step 2
the compound of the formula (5) is transformed to the corresponding hydroxyl compound of formula (2) by treatment with a base, for instance an alkali metal carbonate, e.g. sodium carbonate or potassium carbonate, in particular sodium carbonate.

Interesting accordingly also is a process for the preparation of a compound of the formula (1) or (1A) as defined above, in which process step 1
a compound of formula (4)

(4)

wherein $R_1$ and $R_2$ are as defined above;
is treated with bromine without irradiation with lamps to give a the brominated compound of the formula (5)

(5)

wherein $R_1$ and $R_2$ are as defined above; and
in which process step 2
the compound of the formula (5) is transformed to the corresponding hydroxyl compound of formula (2) by treatment with a base, for instance an alkali metal carbonate, e.g. sodium carbonate or potassium carbonate, in particular sodium carbonate; and
in which process step 3
n compounds of the formula (2)

(2)

wherein n, $R_1$ and $R_2$ are as defined above,
are reacted with an acid chloride of the formula (3)

(3)

wherein n is as defined above,
in the presence of a base, in particular triethyl amine, to give a compound of the formula (1);
and subsequent crystallization from a solvent to give the compound of the formula (1A).

The compounds of the formula (1A), as already mentioned above, are prepared from the compounds of the formula (1) by crystallisation from an appropriate solvent, such as for example water or acetic acid ethyl ester.

The products of all processes as described above optionally can be purified according to the customary methods known to the person skilled in the art.

The photoinitiator compounds of the present invention provide low migration properties from the cured product. Also the photodecomposition products of the photoinitiator compounds provide said property. The photoinitiators have only low odor and provide an excellent reactivity.

The terms "and/or" or "or/and" in the present context are meant to express that not only one of the defined alternatives may be present, but also several of the defined alternatives together, namely mixtures of different alternatives (substituents).

The term "at least" is meant to define one or more than one, for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process and preparation claims as well.

In accordance with the invention, the compounds of the formula (1) can be used as photoinitiators for the photopolymerization of ethylenically unsaturated compounds or of mixtures which comprise such compounds.

The invention therefore also relates to photopolymerizable compositions comprising
(A) at least one ethylenically unsaturated photopolymerizable compound and
(B) at least one photoinitiator of the formula (1).

The composition may comprise additionally to the component (B) at least one further photoinitiator (C) and/or other customary additives (D).

The unsaturated compounds (A) may contain one or more olefinic double bonds. They may be low molecular weight (monomeric) or higher molecular weight (oligomeric).

Examples of monomers containing a double bond are (meth)acrylic acid and salts thereof, (meth)acrylic acid esters, e.g. alkyl esters such as methyl, ethyl, 2-chloroethyl, N-dimethylaminoethyl, n-butyl, isobutyl, pentyl, hexyl, cyclohexyl, 2-ethylhexyl, octyl, isobornyl [2-exobornyl]ester, phenyl, benzyl and o-, m- and p-hydroxyphenyl ester, hydroxyalkyl esters, e.g. 2-hydroxyethyl, 2-hydroxypropyl, 4-hydroxybutyl, 3,4-dihydroxybutyl or glycerol[1,2,3-propanetriol]ester, epoxyalkyl esters, e.g. glycidyl, 2,3-epoxybutyl, 3,4-epoxybutyl, 2,3-epoxycyclohexyl, 10,11-epoxyundecyl ester, (meth)acrylamides, N-substituted (meth)-acrylamides, e.g. N-methylolacrylamide, N-methylolmethacrylamide, N-ethylacrylamide, N-ethylmethacrylamide, N-hexylacrylamide, N-hexylmethacrylamide, N-cyclohexylacrylamide, N-cyclohexylmethacrylamide, N-hydroxyethylacrylamide, N-phenylacrylamide, N-phenylmethacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide and N-(4-hydroxyphenyl)methacrylamide, IBMAA (N-isobutoxymethylacrylamide), (meth)acrylonitriles, unsaturated acid anhydrides such as itaconic anhydride, maleic anhydride, 2,3-dimethylmaleic anhydride, 2-chloromaleic anhydride, unsaturated esters such as maleic acid esters, phthalic acid esters, itaconic acid esters [methylenesuccinic acid esters], styrenes such as methylstyrene, chloromethylstyrene and o-, m- and p-hydroxystyrene, divinylbenzene, vinyl ethers such as isobutyl vinyl ether, ethyl vinyl ether, 2-chloroethyl vinyl ether, hydroxyethyl vinyl ether, propyl vinyl ether, butyl vinyl ether, isobutyl vinyl ether, octyl vinyl ether and phenyl vinyl ether, vinyl and allyl esters such as vinyl acetate, vinyl acrylate, vinyl chloroacetate, vinyl butyrate and vinyl benzoate, divinyl succinate, diallyl phthalate, triallyl phosphate, vinyl chloride and vinylidene chloride, isocyanurates such as triallyl isocyanurate and tris(2-acryloylethyl) isocyanurate, N-vinyl-heterocyclic compounds such as N-vinylpyrrolidones or substituted N-vinylpyrrolidones, N-vinylcaprolactam or substituted N-vinylcaprolactams, N-vinylcarbazole, N-vinylpyridine.

Further examples of suitable esters are:
diacrylate esters such as 1,6-hexanediol diacrylate (HDDA), ethylene glycol diacrylate, propylene glycol diacrylate, dipropylene glycol diacrylate, tripropylene glycol diacrylate, neopentyl glycol diacrylate, hexamethylene glycol diacrylate and bisphenol A diacrylate, trimethylolpropane triacrylate, trimethylolethane triacrylate, trimethylolpropane trimethacrylate, trimethyllolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having molecular weights of from 200 to 1500, or mixtures thereof.

Frequently also used are acrylic acid esters of alkoxylated alcohols, e.g. glycerol ethoxylate triacrylate, glycerol propoxylate triacrylate, trimethylolpropane ethoxylate triacrylate, trimethyllolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Examples of higher-molecular-weight unsaturated compounds (oligomers, prepolymers) are esters of ethylenically unsaturated mono- or poly-functional carboxylic acids and polyols or polyepoxides, and polymers having ethylenically unsaturated groups in the chain or in side groups such as, for example, unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more of such polymers.

Examples of suitable mono- or poly-functional unsaturated carboxylic acids are acrylic acid, methacrylic acid, crotonic acid, cinnamic acid, maleic acid, fumaric acid, itaconic acid, unsaturated fatty acids such as linolenic acid or oleic acid. Acrylic and methacrylic acid are preferred.

However, saturated di- or poly-carboxylic acids in admixture with unsaturated carboxylic acids may also be used. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc.

As polyols, aromatic and especially aliphatic and cycloaliphatic polyols are suitable. Examples of aromatic polyols are hydroquinone, 4,4'-dihydroxydiphenyl, 2,2-di(4-hydroxyphenyl)-propane, and also novolaks and resols. Examples of polyepoxides are those based on the mentioned polyols, especially aromatic polyols and epichlorohydrin. Also suitable as polyols are polymers and copolymers that contain hydroxyl groups in the polymer chain or in side groups such as, for example, polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of polyurethanes are those composed of saturated diisocyanates and unsaturated diols or unsaturated diisocyanates and saturated diols.

Preference is given to methacrylated epoxy esters, methacrylated polyesters, polyesters carrying vinyl groups, methacrylated polyurethanes, methacrylated polyethers and polyols. Suitable components (A) are also acrylates which have been modified by reaction with primary or secondary amines, as described, for example, in U.S. Pat. No. 3,844,916 of Gaske, in EP 280 222 of Weiss et al., in U.S. Pat. No. 5,482,649 of Meixner et al. or in U.S. Pat. No. 5,734,002 of Reich et al. Such amine-modified acrylates are also termed amine acrylates. Amine acrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley and GENOMER 5275 from Rahn.

Some acrylate binders especially designed for low extractables and odour applications can also be used in the formulation. Such resins are commercially available for example under the tradename Ebecryl LEO resins.

Furthermore, cationically UV-curable compositions may be used as part of component (A) for hybrid cationic/radical UV-curing. Such systems typically comprise aliphatic and/or aromatic epoxides, at least one polyol or polyvinyl polyol or oxetane and also at least one photoinitiator that generates cations. The said epoxides, polyols and polyvinyl polyols are known in the art and commercially available. The customarily used photoinitiators are iodonium and sulfonium salts as described, for example, in U.S. Pat. No. 6,306,555. In addition, ethylenically unsaturated compounds may be added to the said cationically UV-curable compositions It is also possible to add solvents or water to the compositions used in the process according to the invention. Suitable solvents are solvents which are known to the person skilled in the art and are conventional especially in surface-coating technology. Examples are various organic solvents such as, for example, ketones, e.g. methyl ethyl ketone, cyclohexanone; aromatic hydrocarbons, e.g. toluene, xylene or tetramethylbenzene; glycol ethers, e.g. diethylene glycol monoethyl ether, dipropylene glycol diethyl ether; esters, e.g. ethyl acetate; aliphatic hydrocarbons, e.g. hexane, octane, decane; or petroleum solvents, e.g. petroleum ether.

The invention relates also to compositions comprising, as component (A), at least one ethylenically unsaturated photopolymerisable compound dissolved or emulsified in water. Such radiation-curable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The radiation-curable prepolymer or prepolymer mixture is present in concentrations of, for example, from 95 to 20% by weight, especially from 70 to 40% by weight. The sum of the indicated percentages for water and prepolymer in those compositions is in each case 100; auxiliaries and additives, which are present in varying amounts depending on the intended use, are in addition thereto.

The radiation-curable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use prepolymers having higher molecular weights also come into consideration.

Used are, for example, polyesters containing polymerisable C—C double bonds and having an acid number of at most 10, polyethers containing polymerisable C—C double bonds, hydroxyl-group-containing reaction products of a polyepoxide containing at least two epoxide groups per molecule with at least one α,β-ethylenically unsaturated carboxylic acid, polyurethane (meth)acrylates and also acrylic copolymers containing α,β-ethylenically unsaturated acrylic radicals as described, for example, in EP 012 339. Mixtures of those prepolymers may also be used. Also suitable are, for example, the polymerisable prepolymers described in EP 033 896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on particular (meth)acrylic acid alkyl ester polymerisation products are described in EP 041 125; suitable water-dispersible, radiation-curable pre-polymers obtained from urethane acrylates are to be found in, for example, DE 2 936 039.

The photopolymerisable compounds (A) are used singly or in any desired mixture.

Component (A) may also comprise binders, that being especially advantageous when the photopolymerisable compounds are liquid or viscous substances. The amount of the binder may be, for example, from 5 to 95% by weight, preferably from 10 to 90% by weight and especially from 40 to 90% by weight, based on the total solid material. The binder is selected according to the field of use and the properties required therefor such as, for example, developability in aqueous and organic solvent systems, adhesion to substrates and sensitivity to oxygen.

Suitable binders are, for example, polymers having molecular weights of about 5 000-2 000 000, preferably 10 000-1 000 000. Examples are: homo- and co-polymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, e.g. cellulose acetate, cellulose acetate butyrate, methylcellulose, ethylcellulose; polyvinyl butyral, polyvinyl formal, cyclised rubber, polyethers, e.g. polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers, e.g. polycaprolactam and poly(hexamethylene adipamide), polyesters, e.g. poly(ethylene glycol terephthalate) and poly(hexamethylene glycol succinate).

The unsaturated compounds may also be used in admixture with non-photopolymerisable film-forming components. The latter may be, for example, physically drying polymers or solutions thereof in organic solvents, e.g. nitrocellulose or cellulose acetobutyrate, but may also be chemically or thermally curable resins, e.g. polyisocyanates, polyepoxides or melamine resins. Melamine resins are to be understood as including not only condensation products of melamine (=1,3,5-triazine-2,4,6-triamine) but also those of melamine derivatives. In general, the binder is a film-forming binder based on a thermoplastic or thermocurable resin, mainly a thermocurable resin. Examples thereof are alkyd, acrylic, polyester, phenol, melamine, epoxy and polyurethane resins and mixtures thereof. The concomitant use of thermally curable resins is of importance for use in so-called hybrid systems, which are both photopolymerised and also thermally crosslinked.

Component (A) may also comprise film-forming binders based on a thermoplastic or thermocurable resin, mainly a thermocurable resin. Examples thereof are alkyd, acrylic, polyester, phenol, melamine, epoxy and polyurethane resins and mixtures thereof. Examples thereof are described in, for example, Ullmann's Encyclopedia of Industrial Chemistry, 5th Ed., Vol. A18, pp. 368-426, VCH, Weinheim 1991.

The binder may be a binder that fully cures at cold or hot temperatures, for which the addition of a curing catalyst may be advantageous. Suitable catalysts which accelerate full curing of the binder are described in, for example, Ullmann's Encyclopedia of Industrial Chemistry, Vol. A18, p. 469, VCH Verlagsgesellschaft, Weinheim 1991.

WO99/03930; WO2000/010974 and WO2000/020517 of DSM describe maleimide-modified binders. Maleimide-modified binders of that kind may likewise be present.

Examples of binders are:

1. surface-coatings based on cold- or hot-crosslinkable alkyd, acrylate, polyester, epoxy or melamine resins or mixtures of such resins, optionally with the addition of a curing catalyst;

2. two-component polyurethane surface-coating compositions based on hydroxyl-group-containing acrylate, polyester or polyether resins and aliphatic or aromatic isocyanates, isocyanurates or polyisocyanates;
3. two-component polyurethane surface-coating compositions based on thiol-group-containing acrylate, polyester or polyether resins and aliphatic or aromatic isocyanates, isocyanurates or polyisocyanates;
4. single-component polyurethane surface-coating compositions based on blocked isocyanates, isocyanurates or polyisocyanates, which are unblocked during stoving; optionally, the addition of melamine resins is also possible;
5. single-component polyurethane surface-coating compositions based on aliphatic or aromatic urethanes or polyurethanes and hydroxyl-group-containing acrylate, polyester or polyether resins;
6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;
7. two-component surface-coating compositions based on (poly)ketimines and aliphatic or aromatic isocyanates, isocyanurates or polyisocyanates;
8. two-component surface-coating compositions based on (poly)ketimines and an unsaturated acrylate resin or a polyacetoacetate resin or a methacrylamidoglycolate methyl ester;
9. two-component surface-coating compositions based on carboxyl- or amino-group-containing polyacrylates and polyepoxides;
10. two-component surface-coating compositions based on anhydride-group-containing acrylate resins and a polyhydroxy or polyamino component;
11. two-component surface-coating compositions based on acrylate-containing anhydrides and polyepoxides;
12. two-component surface-coating compositions based on (poly)oxazolines and anhydride-group-containing acrylate resins or unsaturated acrylate resins or aliphatic or aromatic isocyanates, isocyanurates or polyisocyanates;
13. two-component surface-coating compositions based on unsaturated (poly)acrylates and (poly)malonates;
14. thermoplastic polyacrylate surface-coating compositions based on thermoplastic acrylate resins or extrinsically crosslinking acrylate resins, in combination with etherified melamine resins;
15. surface-coating systems, especially clearcoats, based on malonate-blocked isocyanates with melamine resins (e.g. hexamethoxymethyl melamine) as crosslinkers (acid-catalysed);
16. UV-curable systems based on oligomeric urethane acrylates and/or acylate acrylates, optionally with the addition of other oligomers or monomers;
17. dual-cure systems, which are first cured thermally and then UV-cured, or vice versa, wherein constituents of the surface-coating composition contain double bonds which can be made to react by UV light and photoinitiators and/or by electron-beam curing.

Both 1-component (1C) and 2-component (2C) systems may be used as binder. Examples of such systems are described in Ullmann's Encyclopedia of Industrial Chemistry, Vol. A18, Paints and Coatings, page 404-407, VCH Verlagsgesellschaft mbH, Weinheim (1991).

The composition can be optimised by specifically modifying the formulation, e.g. by varying the binder/crosslinker ratio. The person skilled in the art of coating or ink technology will be familiar with such measures.

Subject of the invention is photopolymerizable composition as described above, additionally comprising a binder polymer (e), in particular a copolymer of methacrylate and methacrylic acid.

In addition to the photoinitiator, the photopolymerisable mixtures may comprise various additives (D). Examples thereof are thermal inhibitors, which are intended to prevent premature polymerisation, e.g. 2,2,6,6-tetramethyl-4-hydroxy-piperidin-1-oxyl (4-hydroxy-TEMPO) and derivatives thereof, e.g. bis(2,2,6,6-tetramethylpiperidin-1-oxyl-4-yl)-decanedioate or polyalkyl-piperidin-N-oxyl radicals, 3-aryl-benzofuran-2-one and derivatives thereof, e.g. 5,7-di-tert-butyl-3-phenyl-3H-benzofuran-2-one (as described in, for example, WO 01/42313), hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

Examples of such UV absorbers and light stabilisers are disclosed in WO 04/074328, page 12, line 9 to page 14, line 23, said disclosure hereby is incorporated by reference.

Further, additives that are customary in the art such as, for example, antistatics, flow improvers and adhesion promoters may be used.

In accordance with the invention, if the formulation comprises binder, thermal drying or curing catalysts may additionally be added to the formulation as additional additives (D). Possible drying catalysts, or thermal curing catalysts, are, for example, organic metal compounds, amines or/and phosphines. Organic metal compounds are, for example, metal carboxylates, especially those of the metals Pb, Mn, Hf, Co, Zn, Zr or Cu, or metal chelates, especially those of the metals Hf, Al, Ti or Zr, or organometal compounds, such as e.g. organotin compounds. Examples of metal carboxylates are the stearates of Pb, Mn or Zn, the octoates of Co, Zn or Cu, the naphthenates of Mn and Co or the corresponding linoleates or tallates (tall oil, which contains rosin acids, oleic and linoleic acids). Examples of metal chelates are the aluminium, titanium or zirconium chelates of acetyl acetone, ethylacetyl acetate, salicylaldehyde, salicylaldoxime, o-hydroxyacetophenone or ethyl-trifluoroacetyl acetate and the alkoxides of those metals. Examples of organotin compounds are dibutyltin oxide, dibutyltin dilaurate and dibutyltin dioctoate. Examples of amines are especially tertiary amines such as, for example, tributylamine, triethanolamine, N-methyldiethanolamine, N-dimethylethanolamine, N-ethylmorpholine, N-methylmorpholine and diazabicyclooctane (triethylenediamine) and the salts thereof. Further examples are quaternary ammonium salts, such as e.g. trimethylbenzylammonium chloride. It is also possible to use phosphines such as, for example, triphenyl-phosphine, as curing catalysts. Suitable catalysts are also described in, for example, J. Bielemann, Lackadditive, Wiley-VCH Verlag GmbH, Weinheim, 1998, pages 244-247. Examples are carboxylic acids such as, for example, p-toluenesulfonic acid, dodecylbenzenesulfonic acid, dinonylnaphthalenesulfonic acid and dinonylnaphthalenedisulfonic acid. There may also be used, for example, latent or blocked sulfonic acids, it being possible for the blocking of the acid to be ionic or non-ionic.

Such catalysts are used in concentrations customary in the art and known to the skilled person.

In order to accelerate photopolymerisation, amines may be added as further additives (D), especially tertiary amines, e.g. tributylamine, triethanolamine, p-dimethylaminobenzoic acid ethyl ester, Michler's ketone, N-methyl-diethanolamine, N-dimethylethanolamine, N-ethylmorpholine, N-methylmorpholine, diazabicyclooctane (triethylenediamine), 1,8-diazabicyclo-[5.4.0]undec-7-ene (DBU), 1,5-diazabicyclo[4.3.0]non-5-ene (DBN) and salts thereof. Further examples are quaternary ammonium salts, e.g. trimethylbenzylammonium chloride. The action of the amines may be reinforced by adding aromatic ketones of the benzophenone type. Amines that are suitable as oxygen capture agents are, for example, N,N-dialkylanilines as described in EP 339 841. Further accelerators, coinitiators and auto-oxidisers are thiols, thioethers, disulfides and phosphines as described in, for example, EP 438 123 and GB 2 180 358.

It is also possible for chain transfer reagents customary in the art to be added to the compositions according to the invention. Examples are mercaptans, amines and benzothiazole.

Photopolymerisation can also be accelerated by addition, as further additives (D), of photosensitisers, which shift or broaden the spectral sensitivity. These include especially aromatic carbonyl compounds such as, for example, benzophenone derivatives, thioxanthone derivatives, including especially isopropyl thioxanthone, anthraquinone derivatives and 3-acylcoumarin derivatives, terphenyls, styryl ketones, and 3-(aroylmethylene)-thiazolines, camphorquinone and also eosin, rhodamine and erythrosine dyes.

The amines mentioned above, for example, may also be regarded as photosensitisers. Examples of suitable sensitizer compounds (D) are disclosed in WO 06/008251, page 36, line 30 to page 38, line 8, the disclosure of which is hereby incorporated by reference.

The curing process, especially of pigmented (e.g. pigmented with titanium dioxide) compositions, can also be assisted by adding an additional additive (D) which under thermal conditions is a free-radical-forming component, for example an azo compound, e.g. 2,2'-azobis(4-methoxy-2,4-dimethylvaleronitrile), a triazene, a diazo sulfide, a pentazadiene or a peroxy compound such as a hydroperoxide or peroxycarbonate, e.g. tert-butyl hydroperoxide as described in, for example, EP 245 639.

Further customary additives (D) are—depending on the intended use—fluorescent whitening agents, fillers, e.g. kaolin, talc, barite, gypsum, chalk or silicate-type fillers, wetting agents or flow improvers.

For curing thick and pigmented coatings, the addition of glass microspheres or powdered glass fibres is suitable, as described in, for example, U.S. Pat. No. 5,013,768.

The formulations may also comprise dyes and/or white or coloured pigments [as further additive (D)]. Depending on the intended use, both inorganic and organic pigments may be used. Such additives will be known to the person skilled in the art; a few examples are titanium dioxide pigments, e.g. of the rutile or anatase type, carbon black, zinc oxide, e.g. zinc white, iron oxides, e.g. iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments.

The pigments may be used in the formulations singly or in admixture.

The pigments are added to the formulations, in accordance with the intended use, in amounts customary in the art, for example in an amount of from 1 to 60% by weight, or from 10 to 30% by weight, based on the total mass.

The formulations may also comprise, for example, organic dyes from a very wide variety of classes. Examples are azo dyes, methine dyes, anthraquinone dyes or metal complex dyes. Customary concentrations are, for example, from 0.1 to 20%, especially from 1 to 5%, based on the total mass.

Selection of the additives is based on the particular field of use and the properties desired in that field.

Subject of the invention also is a photopolymerizable composition as described above as further additive (D) comprising a pigment or dye or a mixture of pigments or dyes.

The additives (D) described hereinbefore are customary in the art and are accordingly used in amounts customary in the art.

It is, of course, possible to use mixtures of the compound of the invention with known photoinitiators (C), for example mixtures with camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone 4,4'-bis (chloromethyl)benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis (dimethylamino)benzophenone, 4,4'-bis(diethylamino) benzophenone; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)-phenoxy]-phenyl}-2-methyl-propan-1-one; oligomeric α-hydroxy ketones; dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl) aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester;

oximeesters, e.g. 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), or for example a combination of oxime esters with α-amino ketones, e.g. a combination of (4-morpholinobenzoyl)-1-benzyl-1-dimethylaminopropane with [4-(2-methylphenylcarboxy)phenyl]-bis[4-(O-acetyloximine)phenyl]amine; peresters, e.g. benzophenone tetracarboxylic peresters as described for example in EP 126541, monoacyl phosphine oxides, e.g. (2,4,6-trimethylbenzoyl)diphenylphosphine oxide, ethyl (2,4,6-trimethylbenzoyl phenyl) phosphinic acid ester; bisacylphosphine oxides, e.g. bis(2,6-dimethoxy-benzoyl)-(2,4,4-trimethyl-pentyl)-phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5-]triazine, 2-methyl-4,6-bis-trichloromethyl-[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl)titanium. Further, borate compounds can be used as coinitiators.

Many of said additional photoinitiators (C) are commercially available, for example under the tradenames DAROCUR® and IRGACURE® from Ciba Inc.

The photopolymerizable composition as described above for example comprises 0.05 to 15% by weight, preferably 0.1 to 5% by weight, of the photoinitiator (B) or the photoinitiators (B)+(C), based on the composition.

The compositions according to the invention can be used for various purposes, for example in overprint coatings, as printing ink, e.g. screen printing ink, ink for offset- or flexo printing, inkjet ink, ink for sheet-fed printing, electrophotography ink, intaglio ink, as clearcoats, white coats or colour-pigmented coats, e.g. for wood or metal, as powder coatings, as paints, inter alia for paper, wood, metal or plastics, as daylight-curable paints for marking structures and roads, paints for buidings, constructions, vehicles etc., for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by curing in the mass (UV curing in transparent moulds) or according to the stereolithography process, as described in, for example, U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical apparatus, aids or implants. The compositions can also be used for the preparation of gels having thermotropic properties. Such gels are described in, for example, DE 197 00 064 and EP 678 534.

Photocuring further is of great importance for printing applications, since the drying time of the ink is a critical factor for the production rate of graphic products, and should be in the order of fractions of seconds. UV-curable inks are particularly important for screen printing, offset inks, ink-jet inks, flexographic printing inks, intaglio inks, electrophotographic inks, sheetfed inks, overprint varnishes or primers.

As already mentioned above, the novel photoinitiator mixtures are highly suitable also for producing printing plates e.g. flexo printing plates or offset printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Printing inks are known to the person skilled in the art, are used widely in the art and are described in the literature.

They are, for example, pigmented printing inks and printing inks coloured with dyes.

A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks. Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 15% by weight, based on the total weight of the printing ink.

The printing inks can be used, for example, for intaglio printing, gravure printing, flexographic printing, screen printing, offset printing, lithography or continuous or dropwise ink-jet printing on material pretreated in accordance with the process of the invention using generally known formulations, for example in publishing, packaging or shipping, in logistics, in advertising, in security printing or in the field of office equipment.

Suitable printing inks are both solvent-based printing inks and water-based printing inks. Of interest are, for example, printing inks based on aqueous acrylate. Such inks are to be understood as including polymers or copolymers that are obtained by polymerisation of at least one monomer containing a group and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry oxidatively.

The printing inks are dried in a known manner customary in the art, optionally with heating of the coating.

A suitable aqueous printing ink composition comprises, for example, a pigment or a combination of pigments, a dispersant and a binder.

Subject of the invention therefore also is a photopolymerizable composition as described above as further additive (D) comprising a dispersant or a mixture of dispersants.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids. Such dispersants are known and are described, for example, in U.S. Pat. No. 5,186,846 and DE-A-197 27 767. Suitable oxalkylated phenols are likewise known and are described, for example, in U.S. Pat. No. 4,218,218 and DE-A-197 27 767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol.

It is also possible, for example, to use polymeric acids which act both as dispersants and as binders.

Examples of suitable binder components that may be mentioned include (meth-)acrylate-group-containing, vinyl-group-containing and/or, depending on the intended application, epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP-A-704 469, EP-A-12 339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≤1% by weight, based on the weight of the preparation.

Printing inks include, for example, those comprising a dye (with a total content of dyes of e.g. from 1 to 35% by weight, based on the total weight of the ink). Dyes suitable for colouring such printing inks are known to the person skilled in the art and are widely available commercially, e.g. from Ciba Spezialitatenchemie AG, Basel.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_6$alkylene glycols and thioglycols, further polyols, e.g. glycerol and $C_1$-$C_4$alkyl ethers of polyhydric alcohols, usually in an amount of from 2 to 30% by weight, based on the total weight of the printing ink.

The printing inks may also, for example, comprise solubilisers, e.g. ∈-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed. Suitable substrates are, for example, textile fibre materials, paper, plastics or aluminium foils pretreated by the process according to the invention. Suitable recording systems are e.g. commercially available ink-jet printers.

Preference is given to printing processes in which aqueous printing inks are used.

Preferred in ink-jet ink formulations comprise (meth)acrylated epoxy esters; (meth)acrylated polyesters or vinyl-ether-group-containing polyesters, (meth)acrylated polyurethanes, polyethers and polyols.

A preferred component used in UV-curable inkjet are acrylates which have been modified by reaction with primary or secondary amines, as described, for example, in U.S. Pat. No. 3,844,916, EP280222, U.S. Pat. No. 5,482,649 or U.S. Pat. No. 5,734,002. Such amine-modified acrylates are also termed aminoacrylates. Examples are already given hereinbefore. It is known that in the presence of aminoacrylates UV-curable systems show an increased curing performance. They are useful to overcome the oxygen inhibition typically observed for radical induced polymerization reactions, especially for low viscous systems like UV-curable inkjet.

It will be clear that mixtures of all these cited monomers, prepolymers, polymers and oligomers can be used in the ink compositions comprising the novel photoinitiator according to the present invention.

The amount of the photopolymerizable monomer, oligomer or prepolymer in this connection is for example 10 to 80 wt %, preferably 10 to 60 wt %.

The inks comprising the photoinitiator of the present invention may besides to radically polymerizable components also comprise cationic-curable compositions having a low viscosity which comprise at least one aliphatic or aromatic epoxide, at least one polyol or polyvinyl polyols as mentioned above, and at least one cation-generating photoinitiator. A number of these epoxides are well known in the art and are commercially available. Photoinitiators that can be used in the cationic photocurable compositions are, for example, aryl iodonium salts and aryl sulfonium salts.

Emphasized are such hybrid systems that contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins. Examples are also as given above.

Furthermore interesting are hybrid systems that are photopolymerized in a first stage and then crosslinked through thermal post-treatment in a second stage or vice versa. Such hybrid systems comprise an unsaturated compound in admixture with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins.

Other compositions suitable as for example ink-jet inks are dual cure compositions, which are cured first by heat and subsequently by UV or electron irradiation, or vice versa, and whose components contain ethylenic double bonds as described above capable to react on irradiation with UV light in presence of a photoinitiator, in the context of the invention the novel photoinitiator of formula (1) as described above.

Ink jet inks for example contain a colorant. A wide variety of organic and inorganic dyes and pigments, alone or in combination may be selected for use in ink jet ink compositions; the person skilled in the art is familiar with the appropriate choice. The pigment particles should be sufficiently small (0.005 to 15 µm) to permit free flow of the ink at the ejecting nozzles. The pigment particles should preferably be 0.005 to 1 µm.

Very fine dispersions of pigments and their preparation are disclosed in e.g. U.S. Pat. No. 5,538,548. The inks preferably comprise a total content of colorant of 1 to 35% by weight, in particular 1 to 30% by weight, and preferably 1 to 20% by weight, based on the total weight of ink. A limit of 2.5% by weight, in particular 5% by weight, and preferably 7.5% by weight, is preferred here as the lower limit.

Suitable colorants are for example pure pigment powders such as Cyan IRGALITE® Blue GLO (Ciba Inc.) or pigment preparations such as MICROLITH-pigment preparations. Ink jet inks may include a variety of further additives such as for example surfactants, biocides, buffering agents, anti-mold agents, pH adjustment agents, electric conductivity adjustment agents, chelating agents, anti-rusting agents, polymerisation inhibitors, light stabilizers, and the like. Such additives may be included in the ink jet inks in any effective amount, as desired.

A preferred field of use comprises overprint coatings and also pigmented thin coatings (layer thickness <20 µm), for example printing inks that are used in printing methods such as, for example, flexographic printing, offset printing, screen printing, intaglio printing, gravure printing, letterpress printing, tampon printing and inkjet printing.

Overprint coatings typically comprise ethylenically unsaturated compounds such as oligomeric and/or monomeric acrylates. Amine acrylates may also be included.

As mentioned hereinbefore, the overprint coatings and printing inks may also comprise further photoinitiators and coinitiators.

Subject of the invention therefore also is a photopolymerizable composition as described above, which is a printing ink, in particular an offset printing ink.

The photoinitiator of formula (1) according to the invention is also suitable for use in UV-curable adhesives; e.g. in the preparation of pressure-sensitive adhesives, laminating adhesives, hot-melt adhesives, moisture-cure adhesives, silane reactive adhesives or silane reactive sealants and the like, and related applications. Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

The compounds according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, fumarates, vinyl ethers, (meth)acrylates, (meth)acrylamides and mixtures thereof. A free-radical UV-curable powder coating may be formulated by mixing unsaturated polyester resins with solid acrylamides (e.g. methylacrylamido-glycolate methyl ester) and a free-radical photoinitiator according to the invention, for example as described in the lecture "Radiation Curing of Powder Coating", Conference Proceedings, Radtech Europe 1993 by M. Wittig and Th. Gohmann. Free-radical UV-curable power coatings may also be formulated by mixing unsaturated polyester resins with solid acrylates, methacrylates or vinyl ethers and a photoinitiator (or photoinitiator mixture) according to the invention. The powder coatings may also comprise binders, as described in, for example, DE 4 228 514 and EP 636 669. The powder coating formulations described in EP 636 669 comprise, for example, a) an unsaturated resin from the group of (semi-)crystalline or amorphous unsaturated polyesters, unsaturated polyacrylates or mixtures thereof with unsaturated polyesters, with special preference being given to those derived from maleic acid or fumaric acid; b) an oligomeric or polymeric crosslinking agent containing vinyl ether-, vinyl ester- or (meth)acrylate-functional groups, with special preference being given to vinyl ether oligomers, for example divinyl ether-functionalised urethanes; c) the photoinitiator.

The UV-curable powder coatings may also comprise white or coloured pigments. Accordingly, for example, there may preferably be used rutile titanium dioxide in concentrations of up to 50% by weight in order to obtain a cured powder coating with good hiding power. The process normally comprises electrostatic or tribostatic spraying of the powder onto the substrate, e.g. metal or wood, melting of the powder as a result of heating and, after a smooth film has been formed, radiation-curing of the coating using ultraviolet and/or visible light, for example using medium-pressure mercury lamps, metal halide lamps or xenon lamps. A particular advantage of radiation-curable powder coatings compared to corresponding thermally curable coatings is that the flow time after melting of the powder particles can be extended as desired in order to ensure the formation of a smooth high-gloss coating. In contrast to thermally curable systems, radiation-curable powder coatings can be formulated so that they melt at relatively low temperatures, without the undesirable effect of a reduction in shelf-life. For that reason they are also suitable as coatings for heat-sensitive substrates, for example wood or plastics. However, if the powder coatings are to be applied to non-heat-sensitive substrates, for example metals (vehicle coatings), it is also possible to make available "dual cure" powder coating formulations using the photoinitiators according to the invention. Such formulations will be known to the person skilled in the art; they are cured both thermally and also by means of UV and can be found in, for example, U.S. Pat. No. 5,922,473.

The compounds according to the invention may also be used in the form of an aqueous, for example 0.5-5%, preferably 0.5-2%, dispersion in polymer dispersions, for example in aqueous polyurethane dispersions, so-called PUDs.

The photocurable compositions according to the invention are suitable, for example, as coating substances for substrates of all kinds, e.g. wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which a protective layer or, by means of imagewise exposure, an image is to be applied.

The substrates can be coated by applying a liquid composition, a solution or a suspension or a powder to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents are, for example, ketones, ethers and esters, e.g. methyl ethyl ketone, isobutyl methyl ketone, cyclopentanone, cyclohexanone, N-methylpyrrolidone, dioxane, tetrahydrofuran, 2-methoxy-ethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by printing methods such as flexography printing, lithography printing, inkjet, screen printing, spin-coating, immersion, roller application, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Ed., Vol. A18, pp. 491-500.

The amount applied (layer thickness) and the nature of the substrate (layer support) are dependent on the desired field of use.

A further field of use comprises compositions that are suitable for the coating of glass fibres, both for the inner and also for the middle and outer layers. The coated glass fibres may also be gathered into bundles giving a further coating. Such coating layers comprise UV-curable oligomers, UV-curable monomers and also at least one photoinitiator and additives. Any UV-curable oligomer is suitable for the coating of glass fibres.

Further fields of use of photocuring are metal coating, for example the application of a finish to sheet metals and tubes, cans or bottle closures, and also photocuring on plastics coatings, for example PVC-based floor or wall coverings.

Examples of the photocuring of paper coatings are the application of a colourless finish to labels, packaging materials or book covers.

The photosensitivity of the compositions according to the invention usually extends from approximately 150 nm into the IR range. Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED), electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible and infrared or NIR range may also be used.

As already mentioned, curing in the process according to the invention can be carried out solely by irradiation with electromagnetic radiation. Depending on the composition of the formulation to be cured, however, thermal curing before, during or after the irradiation is advantageous.

Thermal curing is carried out by methods known to the person skilled in the art. In general, the curing is carried out in an oven, e.g. a circulating air oven, on a heating plate or by irradiation with IR lamps. Unassisted curing at room temperature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The invention relates to the use of the compounds of formula (1) as photoinitiators for the photopolymerization of compositions comprising compounds containing ethylenically unsaturated double bonds and to a process for the photopolymerization of compounds containing ethylenically unsaturated double bonds, which comprises irradiating a composition as described above with electromagnetic radiation in the range from 150 to 600 nm, or with electron beam or with X-rays.

Another subject of the invention is the use of the composition as described above for producing pigmented and non-pigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board; as well as a process as described above for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereo-lithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board.

Preferred is a process as described above for the production of pigmented and non-pigmented surface coatings, overprint coatings, powder coatings, printing inks, inkjet inks, gel coats, composite materials or glass fibre coatings; as well as the use of the compositions as described above for the production of pigmented and non-pigmented surface coatings, overprint coatings, powder coatings, printing inks, inkjet inks, gel coats, composite materials or glass fibre coatings.

The invention relates also to a coated substrate which is coated on at least one surface with a composition as described above.

In particular of interest is the use of a composition as described above as a surface coating for food packaging materials, as well as a process as described above for the production of a surface coating for food packaging materials employing a composition as described above.

The examples which follow illustrate the invention in more detail. Parts and percentages are, as in the remainder of the description and in the claims, by weight, unless stated otherwise.

PREPARATION EXAMPLES

Example 1

1-(4-{Bromo-[4-(2-chloro-2-methyl-propionyl)-phenyl]-methyl}-phenyl)-2-chloro-2-methyl-propan-1-one

(the numbering corresponds to NMR assignments, not name)
$C_{21}H_{21}BrCl_2O_2$, MW=456.21

A 350 ml sulfonation flask fitted with stirrer, reflux condenser and pressure equalized dropping funnel is charged with 2-chloro-1-{4-[4-(2-chloro-2-methyl-propionyl)-benzyl]-phenyl}-2-methyl-propan-1-one (113.1 g, 0.3 mol) and ortho-dichlorobenzene (150 ml). The mixture is heated to 150° C., and then a solution of bromine (49.6 g, 0.3 mol) in ortho-dichlorobenzene (50 ml) is added slowly in such a way that the bromine is reacted before the addition of the next drop of the bromine solution. When all the bromine has been added, the mixture is kept at 150° C. for another ten minutes, and then the ortho-dichlorobenzene is carefully removed on the rotavapor. The residue is recrystallized from hexanes to give the product (116.3 g, 85% of theory) as off white crystals, mp.=93° C. $^1$H-NMR (CDCl$_3$, 400 MHz) δ 1.89 (s, 12 H, CH$_3$); 6.29 (s, 1 H, CH); 7.54 (m, 4 H, H-4); 7.73 (m, 4 H, H-3). $^{13}$C-NMR (CDCl$_3$, 100 MHz) δ 30.47 (C-8); 52.82 (C-1), 68.30 (C-7) 128.22 (C-3), 130.57 (C-4), 134.19 (C-5); 144.54 (C-2); 198.26 (C-6).

Example 2

2-Hydroxy-1-(4-{hydroxy-[4-(2-hydroxy-2-methyl-propionyl)-phenyl]-methyl}-phenyl)-2-methyl-propan-1-one

(the numbering corresponds to NMR assignments, not name)

A mixture of the product from Example 1 (20 g, 43.8 mmol), acetone (100 ml), water (100 ml), and sodium carbonate (10.0 g, 94.3 mmol) is stirred at 60° C. for 60 h. Then the acetone is removed on the rotavapor, and to the residue is added water (50 ml). The product is extracted with ethyl acetate. After drying the organic layer with sodium sulfate, removal of the solvent gives a colorless solid (15.7 g), which is re-dissolved in tert.butyl methyl ether (TBME) and then filtered through a pad of Hyflo. The solvent is removed on the rotavapor until ca. 50 g material remains in the flask, and then hexane is added carefully under efficient stirring until the mixture becomes turbid. After formation of crystals some more hexane is added to bring about crystallization of the product which is filtered off and dried. Yield 11.32 g (72.5%), mp.=130° C. $^1$H-NMR (CDCl$_3$, 300 MHz) δ 1.56 (s, 12 H, H-8); 3.63 (br s, 2 H, OH); 5.87 (s, C-1); 7.44 ("d", 4 H, H-3); 7.96 ("d", 4 H, H-4). $^{13}$C-NMR (CDCl$_3$, 75 MHz) δ 28.70 (C-8); 75.45 (C-1); 76.76 (C-7); 126.63 (C-3); 130.34 (C-4); 133.34 (C-5); 148.23 (C-2); 204.19 (C-6).

Example 3a

[4-(2-hydroxy-2-methylpropionyl)phenyl]methanol, the compound of example 2, (9.35 g, 26 mmol) are dissolved in 25 ml of anhydrous tetrahydrofuran (THF) at 0° C. under argon atmosphere. Triethylamine (2.92 g, 29 mmol) is added, followed by a solution of 2.66 g (13 mmol) of terephthaloyl chloride in 5 ml THF (dropwise addition over 2 h). After stirring for 18 h in an ice bath, the reaction mixture is poured onto iced water and extracted with ethyl acetate. The organic extracts are washed to pH 7 with water, dried over MgSO$_4$ and rotary evaporated to yield 7.15 g of terephthalic acid bis-{bis-[4-(2-hydroxy-2-methyl-propionyl)-phenyl]-methyl}ester as an off-white amorphous solid. The compound is identified by NMR:

(the numbering corresponds to NMR assignments, not name)
C$_{50}$H$_{50}$O$_{12}$ MW=842.95
$^1$H-NMR (CDCl$_3$, 300 MHz) δ (ppm) 1.62 (s, 24 H, H-8); 3.83 (s, 4 H, OH); 7.18 (s, 2 H, H-1); 7.55 ("d", 8 H, H-3); 8.07 ("d", 8 H, H-4); 8.26 (s, 4 H, H-11).
$^{13}$C-NMR (CDCl$_3$, 100 MHz) δ 28.37 (C-8); 76.54 (C-7); 76.93 (C-1); 127.00 (C-3); 130.00 (C-11); 130.31 (C-4); 133.87, 133.95 (C-5*, C-10*); 143.74 (C-2); 164.37 (C-9); 203.91 (C-6).

Figure 1:
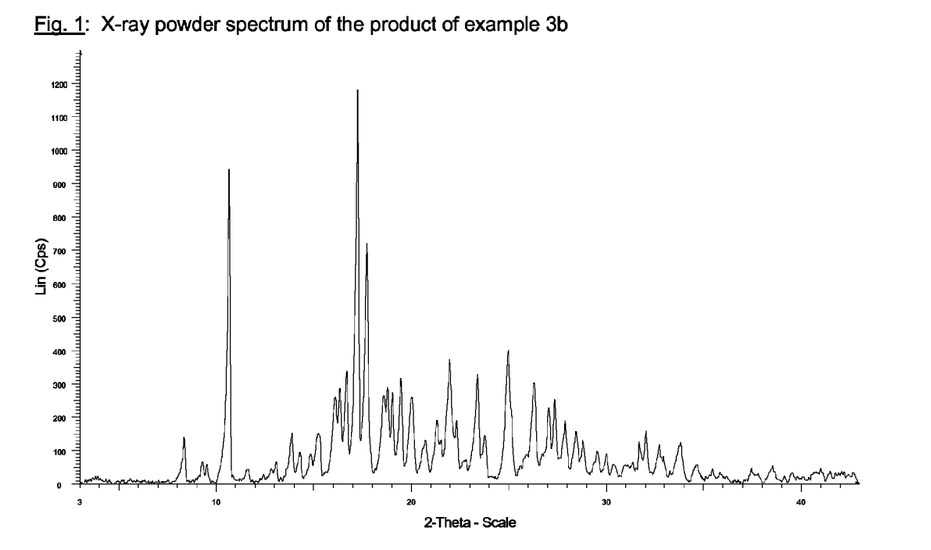
FIG. 1 is an X-ray powder spectrum of terephthalic acid bis-{bis-[4-(2-hydroxy-2-methyl-propionyl)-phenyl]-methyl} ester solvate with 2 molecules of ethyl acetate, white crystals, m.p. 102° C., the product of Example 3b.

Example 3b 16.2 g of the amorphous product of example 3a are dissolved in 25 g of refluxing ethyl acetate and slowly cooled to room temperature. A small amount of hexanes is added, and the mixture is left overnight under stirring. After adding some more hexanes and cooling to 0° C., the crystallized product is filtered and dried between 20° C. and 50° C. under vacuum. 14.8 g of terephthalic acid bis-{bis-[4-(2-hydroxy-2-methyl-propionyl)-phenyl]-methyl}ester, solvate with 2 molecules of ethyl acetate, are obtained as white crystals, m.p. 102° C. The stoechiometry of the solvate is deduced from the NMR spectrum and remains constant upon further drying. The X-ray powder spectrum shows lines characteristic of a crystalline structure (FIG. 1)

Figure 2:
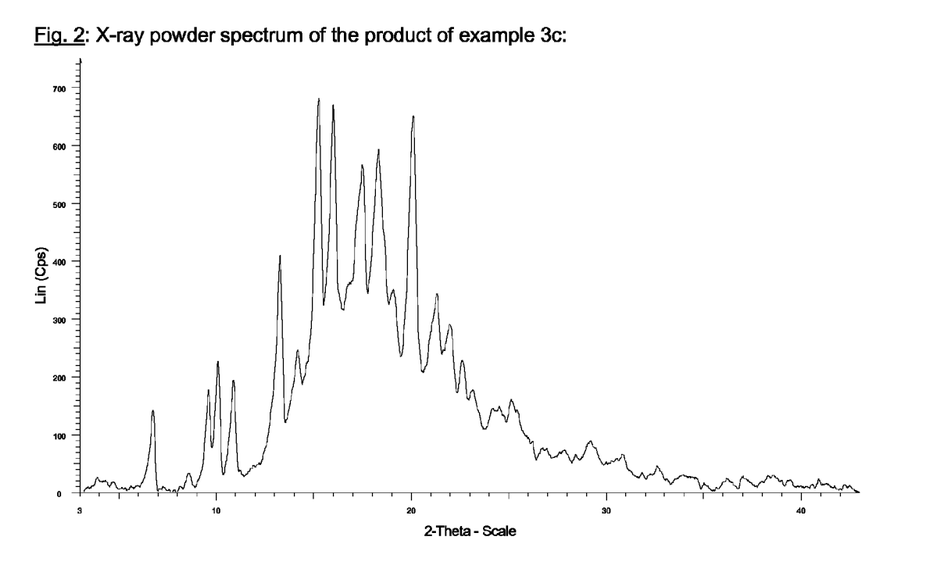
FIG. 2 is an X-ray powder spectrum of crystalline, solvent-free terephthalic acid bis-{bis-[4-(2-hydroxy-2-methyl-propionyl)-phenyl]-methyl} ester, m.p. 105° C., the product of Example 3c. The lines in the X-ray powder spectrum show that the crystal lattice is different from the one of Example 3b (FIG. 2).

Example 3c 3.27 g of the crystalline solvate product of example 3b are suspended in anhydrous ethanol and heated to reflux during 2 hours without complete dissolution. After cooling, 1.76 g of a white powder are obtained by filtration and vacuum-dried at 50° C. The product consists of crystalline, solvent-free terephthalic acid bis-{bis-[4-(2-hydroxy-2-methyl-propionyl)-phenyl]-methyl}ester, m.p. 105° C. The NMR-Spectrum confirms the absence of ethyl acetate. The lines in the X-ray powder spectrum shows that the crystal lattice is different from the one of example 3b (FIG. 2).

Examples 4-5

The compounds of examples 4 and 5 and their physical data are collected in the following table. They are prepared from the compound of example 2 according to the method of example 3 and purified by column chromatography on silica, using dichloromethane/ethanol 95/5 as eluent.

| Ex. | Structure | physical data |
|---|---|---|
| 4 | (structure) | Colorless amorphous solid. $^1$H-NMR (CDCl$_3$, 300 MHz) δ (ppm) 1.60 (s, 36 H); 3.79 (s, 6 H, OH); 7.17 (s, 3 H); 7.53 ("d", 12 H); 8.08 ("d", 12 H,); 9.05 (s, 3 H) Elemental Analysis: C$_{72}$H$_{72}$O$_{18}$ = 1225.37 g/mol. Calc: C 70.58%, H: 5.92%, O: 23.5%; Found: C: 69.75%, H: 6.03%, O: 22.94% |
| 5 | (structure) | Colorless amorphous solid. $^1$H-NMR (CDCl$_3$, 300 MHz) δ (ppm) 1.59 (s, 24 H); 4.13 (br.s, 4 H, OH); 7.16 (s, 2 H); 7.53 ("d", 8 H); 7.64 ("t", 1H), 8.08 ("d", 8 H,) ; 8.37 ("d", 2 H), 8.88 (m, 1 H) |

APPLICATION EXAMPLES

Example A1

Formulations 1 and A are prepared by mixing the following ingredients:

Formulation 1:

| Parts in weight | Trade name | Product type | Supplier |
|---|---|---|---|
| 30% | EBECRYL 605 | Bisphenol A epoxyacrylate diluted with 25% of TPGDA | Cytec |
| 10% | EBECRYL 7100 | Amine modified acrylate | Cytec |
| 5% | EBECRYL 40 | Propoxylated/ethoxylated pentaerythritol tetraacrylate | Cytec |
| 30% | OTA 480 | Propoxylated glycerol triacrylate | Cytec |
| 24% | TPGDA | Tripropyleneglycol diacrylate | Cytec |
| 0.5% | EBECRYL 1360 | Silicone hexaacrylate | Cytec |
| 0.5% | Dow Corning 57 | Silicone additive | Dow Corning |

Formulation A:

| Parts in weight | Product type |
|---|---|
| 5% | the compound of example 3a |
| 95% | Formulation 1 |

Formulation A is applied onto a coilcoat by means of a bar coater to provide a film thickness around 6 μm. Films are further exposed to a medium pressure mercury lamp with aluminium reflectors at 200 W/cm under air at different belt speeds. A Tela tissue is used to rub the surface of the films, a visible trace at the film surface characterizes a poor curing of the ink surface whereas no visible trace means that the film is well cured. Cure speed is defined as the maximum belt speed required to obtain a proper curing under those conditions. The coating is well cured at a belt speed of 60 m/min.

Example A2

Formulations 2 and B are prepared by mixing the following ingredients:
Formulation 2

| Parts in weight | Trade name | Product type | Supplier |
| --- | --- | --- | --- |
| 45% | EBECRYL 605 | Bisphenol A epoxyacrylate diluted with 25% of TPGDA | Cytec |
| 18% | SR 454 | Ethoxylated trimethylolpropane triacrylate | Sartomer |
| 27% | SR 508 | Dipropylene glycol diacrylate | Sartomer |
| 10% | EBECRYL P115 | Amine-functional acrylate | Cytec |

Formulation B:

| Parts in weight | Product type |
| --- | --- |
| 5% | the compound of example 3a or 3b |
| 95% | Formulation 2 |

The products of examples 3a and 3b are completely dissolved in formulation B after stirring for 1 hour at 60° C. Application and test methods are identical with those of Application example A1. Both products show the same reactivity of 70 m/min (belt speed) in the dry-rub resistance test.

The invention claimed is:

1. A compound of formula (1) or (1A)

(1)

(1A)

wherein $R_1$ and $R_2$ are methyl or together are —$(CH_2)_5$—; and n is 2 or 3 and the solvent in (1A) is water or an organic solvent.

2. A compound of the formula (1) or (1A) according to claim 1, wherein $R_1$ and $R_2$ are methyl.

3. A photopolymerizable composition, comprising (A) at least one ethylenically unsaturated photopolymerizable compound and (B) at least one photoinitiator of the formula (1) or (1A) as defined in claim 1.

4. A photopolymerizable composition according to claim 3, which additionally comprises at least one further photoinitiator (C) and/or other customary additives (D).

5. A photopolymerizable composition according to claim 3, comprising 0.05 to 15% by weight of the at least one photoinitiator (B), based on the composition.

6. A photopolymerizable composition according to claim 4, comprising (D) a pigment or dye or a mixture of pigments or dyes.

7. A photopolymerizable composition according to claim 4, comprising (D) a dispersant or a mixture of dispersants.

8. A photopolymerizable composition according to claim 3 additionally comprising a binder polymer (E).

9. A photopolymerizable composition according to claim 3 which is a printing ink.

10. Process for the preparation of a compound of the formula (1) or (1A) as defined in claim 1, which comprises reacting n compounds of formula (2)

(2)

with an acid chloride of formula (3), in the presence of a base, to give a compound of the formula (1);

and subsequent crystallization from a solvent to give a compound of the formula (1A), wherein $R_1$, $R_2$ and n are as defined in claim 1.

11. Process for the preparation of a compound of formula (2), in which process
step 1) a compound of formula (4)

is treated with bromine without irradiation with lamps or the need to add radical initiators to give a brominated compound of formula (5)

and
step 2) the compound of the formula (5) is transformed to the corresponding hydroxyl compound of formula (2) by treatment with a base,
wherein
$R_1$ and $R_2$ are methyl or together are —$(CH_2)_5$—.

12. Process for the preparation of a compound of the formula (1) or (1A) as defined in claim 1, in which process
step 1) a compound of formula (4)

is treated with bromine without irradiation with lamps to give a brominated compound of formula (5)

and
step 2) the compound of the formula (5) is transformed to the corresponding hydroxyl compound of formula (2) by treatment with a base; and step 3) n compounds of the formula (2)
are reacted with an acid chloride of the formula (3), in the presence of a base, to give a compound of the formula (1); and subsequent crystallization from a solvent to give the compound of the formula (1A),
wherein n, $R_1$ and $R_2$ are as defined claim 1.

13. A process for the photopolymerization of compounds containing ethylenically unsaturated double bonds, which comprises irradiating a composition according to claim 3 with electromagnetic radiation in the range from 150 to 600 nm or with electron beam or with X-rays.

14. A process according to claim 13 for producing pigmented or nonpigmented paints or varnishes, powder coatings, printing inks, printing plates, adhesives, dental compositions, gel coats, photoresists for electronics, electroplating resists, etch resists, liquid or dry films, solder resists, resists to manufacture color filters for display applications, resists to generate structures in the manufacturing processes of plasma-display panels, electroluminescence displays, spacers for LCD, holographic data storage (HDS), compositions for encapsulating electrical or electronic components, magnetic recording materials, micromechanical parts, waveguides, optical switches, plating masks, etch masks, colour proofing systems, glass fibre cable coatings, screen printing stencils, three-dimensional objects by means of stereolithography, image recording materials, holographic recordings, micro-electronic circuits, decolorizing materials, image recording materials using microcapsules, photoresist materials for UV or visible laser direct imaging systems or photoresist materials used for forming dielectric layers in a sequential build-up layer of a printed circuit board.

15. A coated substrate which is coated on at least one surface with a composition according to claim 3.

16. A photopolymerizable composition according to claim 3 which is a surface coating for food packaging materials.

* * * * *